US007205118B2

(12) United States Patent
Tacke et al.

(10) Patent No.: US 7,205,118 B2
(45) Date of Patent: Apr. 17, 2007

(54) NICOTINAMIDE N-METHYLTRANSFERASE AS A MARKER FOR COLORECTAL CANCER

(75) Inventors: Michael Tacke, Munich (DE); Peter Berndt, Basel (CH); Marie-Luise Hagmann, Penzberg (DE); Johann Karl, Peissenberg (DE); Theresa Kott, Munich (DE); Hanno Langen, Steinen (DE); Stefan Palme, Penzberg (DE); Markus Roessler, Germering (DE); Wolfgang Rollinger, Polling (DE); Werner Zolg, Weilhelm-Unterhausen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/152,765

(22) Filed: Jun. 14, 2005

(65) Prior Publication Data

US 2006/0003368 A1 Jan. 5, 2006

Related U.S. Application Data

(63) Continuation of application No. PCT/EP03/14583, filed on Dec. 19, 2003.

(30) Foreign Application Priority Data

Dec. 20, 2002 (EP) .................................. 02028715

(51) Int. Cl.
*G01N 33/53* (2006.01)
(52) U.S. Cl. ....................... 435/7.23; 436/501; 436/518
(58) Field of Classification Search ..................... None
See application file for complete search history.

(56) References Cited

U.S. PATENT DOCUMENTS

| 5,733,748 | A | | 3/1998 | Yu et al. | |
| 5,830,677 | A | | 11/1998 | Wu et al. | |
| 5,939,265 | A | * | 8/1999 | Cohen et al. | .................. 435/6 |

FOREIGN PATENT DOCUMENTS

| WO | WO 95/16919 | | 6/1995 |
| WO | WO 00/12702 | | 3/2000 |
| WO | WO 01/36977 | A2 | 5/2001 |
| WO | WO 01/73027 | A2 | 10/2001 |
| WO | WO 01/96388 | A2 | 12/2001 |
| WO | WO 01/96389 | A2 | 12/2001 |
| WO | WO 01/96390 | A2 | 12/2001 |
| WO | WO 02/12280 | A2 | 2/2002 |
| WO | WO 02/12328 | A2 | 2/2002 |
| WO | WO 02/20986 | A2 | 4/2002 |
| WO | WO 02/078636 | A2 | 10/2002 |
| WO | WO 02/090512 | A2 | 11/2002 |
| WO | WO 2004/057336 | A2 | 7/2004 |

OTHER PUBLICATIONS

Aoyama et al, Neuroscience Letters 298:78-80, Jan. 26, 2001.*
Rozen, Postgrad Med J 77:289-291, May 2001.*
Williams et al, Sem Surg Oncol 8:89-93, 1992.*
Contasta et al, Cancer Biother Radiopham 18:549-557, 2003.*
Ahlquist, D.A. et al., "Fecal Occult Blood Testing for Colorectal Cancer," CGastroenterology Clinics of North America; Colorectal Neoplasia, Part II: Diagnosis & Treatment, vol. 26, No. 1, Mar. 1997, pp. 41-55.
Aksoy, S. et al., "Human Liver Nicotinadime N-Methyltransferase," The Journal of Biological Chemistry, col. 269, No. 20, May 20, 1994, 14835-14840.
Anderson, W.F. et al., "Colorectal Cancer Screening for Persons at Average Risk," Journal of the National Cancer Institute, vol. 94, No. 15, Aug. 7, 2002, pp. 1126-1133.
Aoyama, K. et al, "Nicotinamide-N-methyltransferase is higher in the lumbar cerebrospinal fluid of patients with Parkinson's disease," Neuroscience Letters 298 (2001) 78-80.
Birkenkamp-Demtroder, K. et al., "Gene Expression in Colorectal Cancer," Cancer Research 62, 4352-4363, Aug. 1, 2002.
Bruck, Cl. Et a., "Purification of Mouse Monoclonal Antibodies from Ascitic Fluid by DEAE affi-Gel Blue Chromatography," Methods in Enzymology, vol. 121 (1986) 587-596.
Brünagel, G. et al., "Identification of Nuclear Matrix Protein Alterations Associated with Human Colon Cancer," Cancer Research 62, 2437-2442, Apr. 15, 2002.
Carpelan-Holmström M. et al., "CEA, CA 19-9 and CA 72-4 Improve the Diagnostic Accurary in Gastrointestinal Cancers," Anticancer Research 22;2311-2316 (2002).
Carriquiry, L. Al. et al., "Should Carcinoembryonic Antigen be Used in the Management of Patients with Colorectal Cancer?" Dis Colon Rectum, Jul. 1999, pp. 921-929.
De Marzo, A. M. et al., "Abnormal Regulation of DNA Methyltransferase Expression during Colorecal Carcinogenis," Cancer Research 59, 3855-3860, Aug. 15, 1999.
Galfrè, G. et al., "Preparation of Monoclonal Antibodies: Strategies and Procedures," Methods in Enzymology, vol. 73 (1981) 3-46.
Geenan, J. et al., "Major Complications of Coloscopy: Bleeding and Perforation," Digestive Diseases, vol. 20, No. 3, (Mar. 1975) 231-235.
Goldenberg D. M. et al., "Carcinoembryonic Antigen in Histopathology: Immunoperoxidase Staining of Conventional Tissue Sections," J. Natl Cancer Inst., vol. 57, No. 1, Jul. 1976, pp. 11-22.
Halm, U. et al., "Improved Sensitivity of Fuzzing Logic Based Tumor Marker Profiles for Diagnosis of Pancreatic Carcinoma Versus Benign Pancreatic Disease," Anticancer research 20: 4957-4960 (2000).

(Continued)

*Primary Examiner*—Misook Yu
*Assistant Examiner*—Mark Halvorson
(74) *Attorney, Agent, or Firm*—Marilyn L. Amick; Roche Diagnostics Operations, Inc.

(57) ABSTRACT

The present invention relates to the diagnosis of colorectal cancer. It discloses the use of the protein nicotinamide N-methyltransferase (NNMT) in the diagnosis of colorectal cancer. It relates to a method for diagnosis of colorectal cancer from a liquid sample, derived from an individual by measuring NNMT in said sample. Measurement of NNMT can, e.g., be used in the early detection or diagnosis of colorectal cancer.

3 Claims, 2 Drawing Sheets

OTHER PUBLICATIONS

Herrera, M. A. et al., "Carcinoembryonic Antigen (CEA) as a Prognostic and Monitoring Test in Clinically Complete Resection of Colorectal Carcinoma," Ann. Surg, Jan. 1976, pp. 5-9.

Kassem, H. et al., "A Potential Role of Heat Shcok Proteins and Nicotinamide N-Methyl Transferase in Predicting Response to Radiation in Bladder Cancer," Int. J. Cancer: 101, 454-460 (2002).

Keller, T. et al., "Tumour markers in the diagnosis of bronchial carcinoma: new options using fuzzy logic-based tumour marker profiles," J. Cancer Res Clin Oncol (1998) 124: 565-574.

Martell, R.E. et al., "OVX1 and CEA in patients with colon carcinoma, colon polyps and benign colon disorders," The International Journal of Biological Markers, vol. 13, No. 3, pp. 145-149 (1998).

Moertel, C.G. et al., "An Evaluation of the Carcinoembryonic Antigen (CEA) Test fro Monitoring Patients with Resected Colon Cancer," JAMA, Aug. 25, 1993, vol. 270, No. 8, pp. 943947.

Okamura, A. et al., "Increased Hepatic Nicotinamide N-Methyltransferase Activity as a Marker of Cancer Cachexia in Mice Bearing Colon 26 Adenocarcinoma," Jpn. J. Cancer Res. 89, 649-656, Jun. 1998.

Reynoso, G. et al., "Carcinoembryonic Antigen in Patients with Different Cancers," JAMA, Apr. 17, 1972, vol. 220, No. 3, 361-365.

Silvis, S. E. et al., "Endoscopic Complications; Results of the 1974 American Society for Gastrointestinal Endoscopy Survey," JAMA, Mar. 1, 1976, vol. 235, No. 9, 928-930.

Srinivas, P.R. et al., "Proteomics for Cancer Biomarker Discovery," Clinical Chemistry 48:8, 1160-1169 (2002).

Studier, F.W. et al., "Use of T7 RNA Polymerase to Direct Expression of Cloned Genes," Methods in Enzymology, vol. 185, (1990) 60-89.

Sturgeon, C., "Practice Guidelines for Tumor Marker Use in the Clinic," Clinical Chemistry 48:8 1151-1159 (2002).

Wanebo, H. J. et al., "Preoperative Carcinoembryonic Antigen Level as a Prognostic Indicator I Colorectal Cancer," The New England Journal of Medicine, vol. 299, No. 9, Aug. 31, 1978, 448-451.

Zweig, M. H. et al., "Receiver Operating Characteristic (ROC) Plots: A Fundamental Evaluation Tool in Clinical Medicaine," Clinical Chemistry (1993) 561-577.

UICC International Union Against Cancer, Sobin, L.H. et al. Ch (eds.) TNM, Classification of Malignant Tumours, fifth edition, 1997.

Diamandis, E., Immunoassay, Academic Press, Boston, 1996.

Tijssen, P. Preparation of enzyme-antibody or other enzyme-macromolecule conjugates, Practice and Theory of Enzyme Immunoassays, (1990) 221-278.

* cited by examiner

Tumor sample

Matched control sample

2D-Gels

Magnification of clipping

SEQUENCE LISTING

<160> NUMBER OF SEQ ID NOS: 1

<210> SEQ ID NO 1
<211> LENGTH: 264
<212> TYPE: PRT
<213> ORGANISM: Homo sapiens
<220> FEATURE:
<221> NAME/KEY: MISC_FEATURE
<223> OTHER INFORMATION: Nicotinamide N-methyltransferase (Swiss-PROT: P40261)

<400> SEQUENCE: 1

```
Met Glu Ser Gly Phe Thr Ser Lys Asp Thr Tyr Leu Ser His Phe Asn
1               5                   10                  15

Pro Arg Asp Tyr Leu Glu Lys Tyr Tyr Lys Phe Gly Ser Arg His Ser
            20                  25                  30

Ala Glu Ser Gln Ile Leu Lys His Leu Leu Lys Asn Leu Phe Lys Ile
        35                  40                  45

Phe Cys Leu Asp Gly Val Lys Gly Asp Leu Leu Ile Asp Ile Gly Ser
    50                  55                  60

Gly Pro Thr Ile Tyr Gln Leu Leu Ser Ala Cys Glu Ser Phe Lys Glu
65                  70                  75                  80

Ile Val Val Thr Asp Tyr Ser Asp Gln Asn Leu Gln Glu Leu Glu Lys
                85                  90                  95
```

-continued

```
Trp Leu Lys Lys Glu Pro Glu Ala Phe Asp Trp Ser Pro Val Val Thr
        100                 105             110
Tyr Val Cys Asp Leu Glu Gly Asn Arg Val Lys Gly Pro Glu Lys Glu
        115                 120             125
Glu Lys Leu Arg Gln Ala Val Lys Gln Val Leu Lys Cys Asp Val Thr
    130             135                 140
Gln Ser Gln Pro Leu Gly Ala Val Pro Leu Pro Pro Ala Asp Cys Val
145             150              155                     160
Leu Ser Thr Leu Cys Leu Asp Ala Ala Cys Pro Asp Leu Pro Thr Tyr
            165                 170             175
Cys Arg Ala Leu Arg Asn Leu Gly Ser Leu Leu Lys Pro Gly Gly Phe
            180             185                 190
Leu Val Ile Met Asp Ala Leu Lys Ser Ser Tyr Tyr Met Ile Gly Glu
            195             200                 205
Gln Lys Phe Ser Ser Leu Pro Leu Gly Arg Glu Ala Val Glu Ala Ala
    210             215                 220
Val Lys Glu Ala Gly Tyr Thr Ile Glu Trp Phe Glu Val Ile Ser Gln
225             230                 235                 240
Ser Tyr Ser Ser Thr Met Ala Asn Asn Glu Gly Leu Phe Ser Leu Val
            245                 250                 255
Ala Arg Lys Leu Ser Arg Pro Leu
            260
```

NICOTINAMIDE N-METHYLTRANSFERASE AS A MARKER FOR COLORECTAL CANCER

RELATED APPLICATIONS

This application is a continuation of PCT application PCT/EP03/14583 filed Dec. 19, 2003 and claims priority to European application EP 02028715.7 filed Dec. 20, 2002.

FIELD OF THE INVENTION

The present invention relates to the diagnosis of colorectal cancer. It discloses the use of nicotinamide N-methyltransferase (NNMT) in the diagnosis of colorectal cancer. Furthermore, it especially relates to a method for diagnosis of colorectal cancer from a liquid sample derived from an individual by measuring NNMT in said sample. Measurement of NNMT can, e.g., be used in the early detection or diagnosis of colorectal cancer.

BACKGROUND

Cancer remains a major public health challenge despite progress in detection and therapy. Amongst the various types of cancer, colorectal cancer (CRC) is one of the most frequent cancers in the Western world.

The earlier cancer can be detected/diagnosed, the better is the overall survival rate. This is especially true for CRC. The prognosis in advanced stages of tumor is poor. More than one third of the patients will die from progressive disease within five years after diagnosis, corresponding to a survival rate of about 40% for five years. Current treatment is only curing a fraction of the patients and clearly has the best effect on those patients diagnosed in an early stage of disease.

With regard to CRC as a public health problem, it is essential that more effective screening and preventative measures for colorectal cancer be developed.

The earliest detection procedures available at present for colorectal cancer involve using tests for fecal blood or endoscopic procedures. However, significant tumor size must typically exist before fecal blood is detected. The sensitivity of the guaiac-based fecal occult blood tests is about 26%, which means 74% of patients with malignant lesions will remain undetected (Ahlquist, D. A., Gastroenterol. Clin. North Am. 26 (1997) 41–55). The visualization of precancerous and cancerous lesions represents the best approach to early detection, but colonoscopy is invasive with significant costs, risks, and complications (Silvis, S. E., et al., JAMA 235 (1976) 928–930; Geenen, J. E., et al., Am. J. Dig. Dis. 20 (1975) 231–235; Anderson, W. F., et al., J. Natl. Cancer Institute 94 (2002) 1126–1133).

In the recent years a tremendous amount of so-called colon specific or even so-called colorectal cancer specific genes has been reported. The vast majority of the corresponding research papers or patent applications are based on data obtained by analysis of RNA expression patterns in colon (cancer) tissue versus a different tissue or an adjacent normal tissue, respectively. Such approaches may be summarized as differential mRNA display techniques.

As an example for data available from mRNA-display techniques, WO 01/96390 shall be mentioned and discussed. This application describes and claims more than two hundred isolated polynucleotides and the corresponding polypeptides as such, as well as their use in the detection of CRC. However, it is general knowledge that differences on the level of mRNA are not mirrored by the level of the corresponding proteins. A protein encoded by a rare mRNA may be found in very high amounts and a protein encoded by an abundant mRNA may nonetheless be hard to detect and find at all. This lack of correlation between mRNA-level and protein level is due to reasons like mRNA stability, efficiency of translation, stability of the protein, etc.

There also are recent approaches investigating the differences in protein patterns between different tissues or between healthy and diseased tissue in order to identify candidate marker molecules which might be used in the diagnosis of CRC. Brünagel, G., et al., Cancer Research 62 (2002) 2437–2442 have identified seven nuclear matrix proteins which appear to be more abundant in CRC tissue as compared to adjacent normal tissue. No data from liquid samples obtained from an individual are reported.

WO 02/078636 reports about nine colorectal cancer-associated spots as found by surface-enhanced laser desorption and ionization (SELDI). These spots are seen more frequently in sera obtained from patients with CRC as compared to sera obtained from healthy controls. However, the identity of the molecule(s) comprised in such spot, e.g., its (their) sequence), is not known.

Despite the large and ever growing list of candidate protein markers in the field of CRC, to date clinical/diagnostic utility of these molecules is not known. In order to be of clinical utility a new diagnostic marker as a single marker should be at least as good as the best single marker known in the art. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

At present, only diagnostic blood tests based on the detection of carcinoembryonic antigen (CEA), a tumor-associated glycoprotein, are available to assist diagnosis in the field of CRC. CEA is increased in 95% of tissue samples obtained from patients with colorectal, gastric, and pancreatic cancers and in the majority of breast, lung, and head and neck carcinomas (Goldenberg, D. M., et al., J. Natl. Cancer Inst. (Bethesda) 57 (1976) 11–22). Elevated CEA levels have also been reported in patients with nonmalignant disease, and many patients with colorectal cancer have normal CEA levels in the serum, especially during the early stage of the disease (Carriquiry, L. A., and Pineyro, A., Dis. Colon Rectum 42 (1999) 921–929; Herrera, M. A., et al., Ann. Surg. 183 (1976) 5–9; Wanebo, H. J., et al., N. Engl. J. Med. 299 (1978) 448–451). The utility of CEA as measured from serum or plasma in detecting recurrences is reportedly controversial and has yet to be widely applied (Martell, R. E., et al., Int. J. Biol. Markers 13 (1998) 145–149; Moertel, C. G., et al., JAMA 270 (1993) 943–947).

In light of the available data, serum CEA determination possesses neither sensitivity nor the specificity to enable its use as a screening test for colorectal cancer in the asymptomatic population (Reynoso, G., et al., JAMA 220 (1972) 361–365; Sturgeon, C., Clinical Chemistry 48 (2002) 1151–1159).

Whole blood, serum or plasma are the most widely used sources of sample in clinical routine. The identification of an early CRC tumor marker that would allow reliable cancer detection or provide early prognostic information could lead to a diagnostic assay that would greatly aid in the diagnosis and in the management of this disease. Therefore, an urgent clinical need exists to improve the diagnosis of CRC from blood. It is especially important to improve the early diagnosis of CRC, since for patients diagnosed early on chances of survival are much higher as compared to those diagnosed at a progressed stage of disease.

SUMMARY OF THE INVENTION

The present invention relates to a method for diagnosis of colorectal cancer comprising the steps of providing a liquid sample from a patient, contacting the sample with a specific binding agent for NNMT under conditions appropriate for formation of a complex between the binding agent and NNMT, measuring the amount of complex formed, and correlating the amount of complex formed to the diagnosis of colorectal cancer. The present invention further relates to an immunological kit comprising at least one specific binding agent for NNMT and auxiliary reagents for measurement of NNMT.

DETAILED DESCRIPTION OF THE INVENTION

Figure 1:
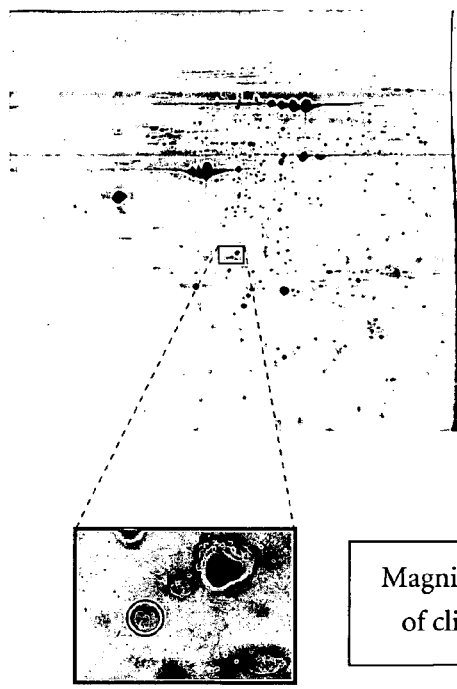
FIG. 1 shows a typical example of a 2D-gel, loaded with a tumor sample (left side), and a gel, loaded with a matched control sample (right side) obtained from adjacent healthy mucosa. The circle in the enlarged section of these gels indicates the position for the protein NNMT. The apparent molecular weight and the isoelectric point of NNMT correspond to the theoretical values of 29.6 kDA and 5.56, respectively. This protein was not detectable by the same method in healthy mucosa.
Figure 1:
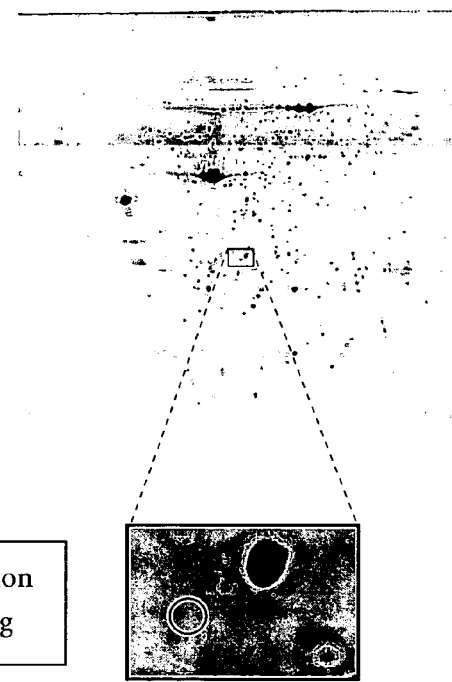
Figure 2:
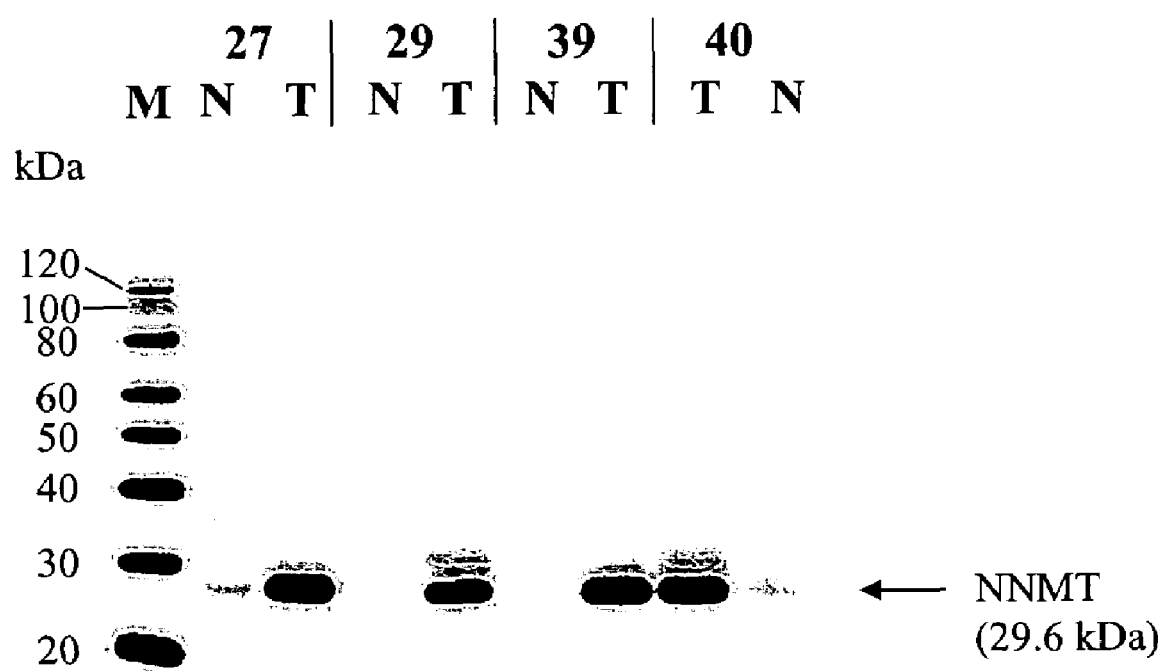
FIG. 2 shows a typical example of a Western-Blot. The gel was loaded with tissue lysates from colorectal tumor tissue and adjacent healthy control tissue from 4 patients (subject 27: rectum ca, Dukes B; subject 29: rectum ca, Dukes A; subject 39: colon ca, Dukes A; and subject 40: colon ca, Dukes B). Presence of NNMT in the samples was tested using a polyclonal rabbit anti-NNMT serum. Lanes containing tumor lysates are indicated with "T", lanes containing normal control tissue with "N". The marker lane containing a molecular weight protein standard is indicated by "M". The arrow indicates the position in the gel of the NNMT band. All tumor samples gave a strong signal at the position of NNMT, whereas almost no signal could be detected in the lysates from adjacent normal control tissue. This strong overexpression of NNMT in tumor tissue from colorectal cancer patients was shown in 14 out of 14 subjects tested.

It was the task of the present invention to investigate whether a new marker can be identified which may aid in CRC diagnosis.

Surprisingly, it has been found that use of the protein NNMT can at least partially overcome the problems known from the state of the art.

The present invention therefore relates to a method for the diagnosis of colorectal cancer comprising the steps of a) providing a liquid sample obtained from an individual, b) contacting said sample with a specific binding agent for NNMT under conditions appropriate for formation of a complex between said binding agent and NNMT, and c) correlating the amount of complex formed in (b) to the diagnosis of colorectal cancer. Thus, it is preferred that the method comprises using a liquid sample obtained from an individual in step (a).

Another preferred embodiment of the invention is a method for the diagnosis of colorectal cancer comprising the steps of a) contacting a liquid sample obtained from an individual with a specific binding agent for NNMT under conditions appropriate for formation of a complex between said binding agent and NNMT, and b) correlating the amount of complex formed in (a) to the diagnosis of colorectal cancer.

The protein nicotinamide N-methyltransferase (Swiss-PROT: P40261) is characterized by the sequence given in SEQ ID NO: 1. NNMT has an apparent molecular weight of 29.6 kDa and an isoelectric point of 5.56.

NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa. (Aksoy, S., et al., J. Biol. Chem. 269 (1994) 14835–14840). Little is known in the literature about a potential role of the enzyme -in human cancer. In one paper, increased hepatic NNMT enzymatic activity was reported as a marker for cancer cachexia in mice (Okamura, A., et al., Jpn. J. Cancer Res. 89 (1998) 649–656). In a recent report, down-regulation of the NNMT gene in response to radiation in radiation sensitive cell lines was demonstrated (Kassem, H., et al., Int. J. Cancer 101 (2002) 454–460).

As obvious to the skilled artisan, the present invention shall not be construed to be limited to the full-length protein NNMT of SEQ ID NO: 1. Physiological or artificial fragments of NNMT, secondary modifications of NNMT, as well as allelic variants of NNMT are also encompassed by the present invention. Artificial fragments preferably encompass a peptide produced synthetically or by recombinant techniques, which at least comprises one epitope of diagnostic interest consisting of at least 6 contiguous amino acids as derived from the sequence disclosed in SEQ ID NO: 1. Such fragment may advantageously be used for generation of antibodies or as a standard in an immunoassay. More preferred the artificial fragment comprises at least two epitopes of interest appropriate for setting up a sandwich immunoassay.

In preferred embodiments, the novel marker NNMT may be used for monitoring as well as for screening purposes.

When used in patient monitoring the diagnostic method according to the present invention may help to assess tumor load, efficacy of treatment and tumor recurrence in the follow-up of patients. Increased levels of NNMT are directly correlated to tumor burden. After chemotherapy a short term (few hours to 14 days) increase in NNMT may serve as an indicator of tumor cell death. In the follow-up of patients (from 3 months to 10 years) an increase of NNMT can be used as an indicator for tumor recurrence.

In a preferred embodiment the diagnostic method according to the present invention is used for screening purposes. That is, it is used to assess subjects without a prior diagnosis of CRC by measuring the level of NNMT and correlating the level measured to the presence or absence of CRC.

Colorectal cancer most frequently progresses from adenomas (polyps) to malignant carcinomas. The different stages of CRC used to be classified according to Dukes' stages A to D.

The staging of cancer is the classification of the disease in terms of extent, progression, and severity. It groups cancer patients so that generalizations can be made about prognosis and the choice of therapy.

Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), Sobin, L. H., Wittekind, Ch. (eds), TNM Classification of Malignant Tumours, fifth edition, 1997).

What is especially important is, that early diagnosis of CRC translates to a much better prognosis. Malignant tumors of the colorectum arise from benign tumors, i.e. from adenoma. Therefore, best prognosis have those patients diagnosed at the adenoma stage. Patients diagnosed as early as in stage $T_{is}$ N0 M0 or T1–3 N0 M0, if treated properly, have a more than 90% chance of survival 5 years after diagnosis as compared to a 5-year survival rate of only 10% for patients diagnosed when distant metastases are already present.

In the sense of the present invention, early diagnosis of CRC refers to a diagnosis at a pre-malignant state (adenoma) or at a tumor stage where no metastases at all (neither proximal nor distal), i.e., adenoma, $T_{is}$ N0 M0 or T1–4 N0 M0 are present. $T_{is}$ denotes carcinoma in situ.

In a preferred embodiment NNMT is used to diagnose CRC as early as in the adenoma stage.

It is further preferred, that CRC is diagnosed when it has not yet fully grown through the bowel wall and thus neither the visceral peritoneum is perforated nor other organs or structures are invaded, i.e., that diagnosis is made at any stage from $T_{is}$ N0 M0 to T3 N0 M0 ($T_{is}$-3 N0 M0).

The diagnostic method according to the present invention is based on a liquid sample which is derived from an individual. NNMT is specifically measured from this liquid sample by use of a specific binding agent.

A specific binding agent is, e.g., a receptor for NNMT, a lectin binding to NNMT or an antibody to NNMT. As the skilled artisan will appreciate the term specific is used to indicate that other biomolecules present in the sample do not significantly bind to the binding agent specific for NNMT. A level of less than 5% cross-reactivity is considered not significant.

A specific binding agent preferably is an antibody reactive with NNMT. The term antibody refers to a polyclonal antibody, a monoclonal antibody, fragments of such antibodies, as well as to genetic constructs comprising the binding domain of an antibody.

Antibodies are generated by state of the art procedures, e.g., as described in Tijssen (Tijssen, P., Practice and theory of enzyme immunoassays 11 (1990) the whole book, especially pages 43–78; Elsevier, Amsterdam). In addition, the skilled artisan is well aware of methods based on immunosorbents that can be used for the specific isolation of antibodies. By these means the quality of polyclonal antibodies and hence their performance in immunoassays can be enhanced. (Tijssen, P., supra, pages 108–115). For the achievements as disclosed in the present invention polyclonal antibodies raised in rabbits have been used. However, clearly also polyclonal antibodies from different species, e.g. rats or guinea pigs, as well as monoclonal antibodies can also be used. Since monoclonal antibodies can be produced in any amount required with constant properties, they represent ideal tools in development of an assay for clinical routine. The generation and use of monoclonal antibodies to NNMT in a method according to the present invention is yet another preferred embodiment.

As the skilled artisan will appreciate now, that NNMT has been identified as a marker which is useful in the diagnosis of CRC, alternative ways may be used to reach a result comparable to the achievements of the present invention. For example, alternative strategies to generate antibodies may be used. Such strategies comprise amongst others the use of synthetic peptides, representing an epitope of NNMT for immunization. Alternatively, DNA immunization also known as DNA vaccination may be used.

For measurement the liquid sample obtained from an individual is incubated with the specific binding agent for NNMT under conditions appropriate for formation of a binding agent NNMT-complex. Such conditions need not be specified, since the skilled artisan without any inventive effort can easily identify such appropriate incubation conditions.

As a final step according to the method disclosed in the present invention the amount of complex is measured and correlated to the diagnosis of CRC. As the skilled artisan will appreciate there are numerous methods to measure the amount of specific binding agent NNMT-complex all described in detail in relevant textbooks (cf., e.g., Tijssen P., supra, or Diamandis et al., eds. (1996) Immunoassay, Academic Press, Boston).

Preferably NNMT is detected in a sandwich type assay format. In such assay a first specific 0binding agent is used to capture NNMT on the one side and a second specific binding agent, which is labeled to be directly or indirectly detectable is used on the other side.

As mentioned above, it has surprisingly been found that NNMT can be measured from a liquid sample obtained from an individual sample. No tissue and no biopsy sample is required to apply the marker NNMT in the diagnosis of CRC.

In a preferred embodiment the method according to the present invention is practiced with serum as liquid sample material.

In a further preferred embodiment the method according to the present invention is practiced with plasma as liquid sample material.

In a further preferred embodiment the method according to the present invention is practiced with whole blood as liquid sample material.

Furthermore stool can be prepared in various ways known to the skilled artisan to result in a liquid sample as well. Such sample liquid derived from stool also represents a preferred embodiment according to the present invention.

Whereas application of routine proteomics methods to tissue samples, leads to the identification of many potential marker candidates for the tissue selected, the inventors of the present invention have surprisingly been able to detect protein NNMT in a bodily fluid sample. Even more surprising they have been able to demonstrate that the presence of NNMT in such liquid sample obtained from an individual can be correlated to the diagnosis of colorectal cancer.

Antibodies to NNMT with great advantage can be used in established procedures, e.g., to detect colorectal cancer cells in situ, in biopsies, or in immunohistological procedures.

Preferably, an antibody to NNMT is used in a qualitative (NNMT present or absent) or quantitative (NNMT amount is determined) immunoassay.

Measuring the level of protein NNMT has proven very advantageous in the field of CRC. Therefore, in a further preferred embodiment, the present invention relates to use of protein NNMT as a marker molecule in the diagnosis of colorectal cancer from a liquid sample obtained from an individual.

The term marker molecule is used to indicate that an increased level of the analyte NNMT as measured from a bodily fluid of an individual marks the presence of CRC.

It is especially preferred to use the novel marker NNMT in the early diagnosis of colorectal cancer.

The use of protein NNMT itself, represents a significant progress to the challenging field of CRC diagnosis. Combining measurements of NNMT with other known markers, like CEA, or with other markers of CRC yet to be discovered, leads to further improvements. Therefore in a further preferred embodiment the present invention relates to the use of NNMT as a marker molecule for colorectal cancer in combination with another marker molecule for colorectal cancer in the diagnosis of colorectal cancer from a liquid sample obtained from an individual. Preferred selected other CRC markers with which the measurement of NNMT may be combined are CEA, CA 19–9, CA 72–4 and/or CA 242.

Diagnostic reagents in the field of specific binding assays, like immunoassays, usually are best provided in the form of a kit, which comprises the specific binding agent and the auxiliary reagents required to perform the assay. The present invention therefore also relates to an immunological kit comprising at least one specific binding agent for NNMT and auxiliary reagents for measurement of NNMT.

Accuracy of a test is best described by its receiver-operating characteristics (ROC) (see especially Zweig, M. H., and Campbell, G., Clin. Chem. 39 (1993) 561–577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results) (number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/ (number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1- specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Clinical utility of the novel marker NNMT has been assessed in comparison to and in combination with the established marker CEA using a receiver operator curve analysis (ROC; Zweig, M. H., and Campbell, G., Clin. Chem. 39 (1993) 561–577). This analysis has been based on well-defined patient cohorts consisting of 50 samples each from patients in T1–3; N0; M0, more progressed tumor, i.e., T4 and/or various severity of metastasis (N+ and/or M+), and healthy controls, respectively.

The diagnostic method based on measurement of NNMT alone in comparison to the established marker CEA alone has been found to have an at least as good a diagnostic accuracy (sensitivity/specificity profile) as demonstrated by the area under the curve.

The examples and figures are provided to aid the understanding of the present invention, the true scope of which is set forth in the appended claims. It is understood that modifications can be made in the procedures set forth without departing from the spirit of the invention.

ABBREVIATIONS

ABTS 2,2'-azino-di- [3-ethylbenzthiazoline sulfonate (6)] diammonium salt
BSA bovine serum albumin
cDNA complementary DNA
CHAPS (3-[(3-cholamidopropyl)-dimethylammonio]-1-propane-sulfonate)
DMSO dimethyl sulfoxide
DTT dithiothreitol
EDTA ethylene diamine tetraacetic acid
ELISA enzyme-linked immunosorbent assay
HRP horseradish peroxidase
IAA iodacetamide
IgG immunoglobulin G
IEF isoelectric focusing
IPG immobilized pH gradient
LDS lithium dodecyl sulfate
MALDI-TOF matrix-assisted laser desorption/ionization time-of-flight mass spectrometry
MES mesityl, 2,4,6-trimethylphenyl
OD optical density
PAGE polyacrylamide gel electrophoresis
PBS phosphate buffered saline
PI isoelectric point
RTS rapid translation system
SDS sodium dodecyl sulfate

EXAMPLE 1

Identification of NNMT as a Potential Colorectal Cancer Marker

Sources of Tissue

In order to identify tumor-specific proteins as potential diagnostic markers for colorectal cancer, analysis of three different kinds of tissue using proteomics methods was performed.

In total, tissue specimen from 10 patients suffering from colorectal cancer were analyzed. From each patient three different tissue types were collected from therapeutic resections: tumor tissue (>80% tumor) (T), adjacent healthy tissue (N) and stripped mucosa from adjacent healthy mucosa (M). The latter two tissue types served as matched healthy control samples. Tissues were immediately snap frozen after resection and stored at −80° C. before processing. Tumors were diagnosed by histopathological criteria.

Tissue Preparation 0.8–1.2 g of frozen tissue were put into a mortar and completely frozen by liquid nitrogen. The tissue was pulverized in the mortar, dissolved in the 10-fold volume (w/v) of lysis buffer (40 mM Na-citrate, 5 mM $MgCl_2$, 1% GENAPOL X-080, 0.02% Na-azide, Complete® EDTA-free [Roche Diagnostics GmbH, Mannheim, Germany, Cat. No. 1 873 580]) and subsequently homogenized in a Wheaton glass homogenizer (20× loose fitting, 20× tight fitting). 3 ml of the homogenate were subjected to a sucrose-density centrifugation (10–60% sucrose) for 1 h at 4500 ×g. After this centrifugation step three fractions were obtained. The fraction on top of the gradient contained the soluble proteins and was used for further analysis.

Isoelectric Focussing (IEF) and SDS-PAGE

For IEF, 3 ml of the suspension were mixed with 12 ml sample buffer (7 M urea, 2 M thiourea, 2% CHAPS, 0.4% IPG buffer pH 4–7, 0.5% DTT) and incubated for 1 h. The samples were concentrated in an Amicon Ultra-15 device (Millipore GmbH, Schwalbach, Germany) and the protein concentration was determined using the Bio-Rad protein assay (Cat. No. 500–0006; Bio-Rad Laboratories GmbH, München, Germany) following the instructions of the supplier's manual. To a volume corresponding to 1.5 mg of protein sample buffer was added to a final volume of 350 µl. This solution was used to rehydrate IPG strips pH 4–7 (Amersham Biosciences, Freiburg, Germany) overnight. The IEF was performed using the following gradient protocol: 1.) 1 minute to 500 V; 2.) 2 h to 3500 V; 3.) 22 h at constant 3500V giving rise to 82 kVh. After IEF, strips were stored at −80° C. or directly used for SDS-PAGE.

Prior to SDS-PAGE the strips were incubated in equilibration buffer (6 M urea, 50 mM Tris/HCl, pH 8.8, 30% glycerol, 2% SDS), for reduction DDT (15 min, +50 mg DTT/10 ml), and for alkylation IAA (15 min,+235 mg iodacetamide/10 ml) was added. The strips were put on 12.5% polyacrylamide gels and subjected to electrophoresis at 1 W/gel for 1 h and thereafter at 17 W/gel. Subsequently, the gels were fixed (50% methanol, 10% acetate) and stained overnight with Novex Colloidal Blue Staining Kit (Invitrogen, Karlsruhe, Germany, Cat. No. LC6025, 45-7101)

Detection of NNMT as a Potential Marker for Colorectal Cancer

Each patient was analyzed separately by image analysis with the ProteomeWeaver software (Definiens AG, Germany, Munich). In addition, all spots of the gel were excised by a picking robot and the proteins present in the spots were identified by MALDI-TOF mass spectrometry (Ultraflex Tof/Tof, Bruker Daltonik GmbH, Bremen, Germany). For each patient, 4 gels from the tumor sample were compared with 4 gels each from adjacent normal and stripped mucosa tissue and analyzed for distinctive spots corresponding to differentially expressed proteins. By this means, protein NNMT was found to be specifically expressed or strongly overexpressed in tumor tissue and not detectable in healthy control tissue. It therefore, amongst many other proteins, qualified as a candidate marker for use in the diagnosis of colorectal cancer.

EXAMPLE 2

Generation of Antibodies to the Colorectal Cancer Marker Protein NNMT

Polyclonal antibody to the colorectal cancer marker protein NNMT was generated for further use of the antibody in the measurement of serum and plasma and blood levels of NNMT by immunodetection assays, e.g. Western Blot and ELISA.

Recombinant Protein Expression in E. Coli

In order to generate antibodies to NNMT, recombinant expression of the protein was performed for obtaining immunogens. The expression was done applying a combination of the RTS 100 expression system and E. coli. In a first step, the DNA sequence was analyzed and recommendations for high yield cDNA silent mutational variants and respective PCR-primer sequences were obtained using the "PROTEOEXPERT RTS E. coli HY" system. This is a commercial web based service. Using the recommended primer pairs, the "RTS 100 E. coli Linear Template Generation Set, His-tag" (Roche Diagnostics GmbH, Mannheim, Germany, Cat. No. 3186237) system to generate linear PCR templates from the cDNA and for in-vitro transcription and expression of the nucleotide sequence coding for the NNMT protein was used. For Western-blot detection and later purification, the expressed protein contained a His-tag. The best expressing variant was identified. All steps from PCR to expression and detection were carried out according to the instructions of the manufacturer. The respective PCR product, containing all necessary T7 regulatory regions (promotor, ribosomal binding site and T7 terminator) was cloned into the pBAD TOPO vector (invitrogen, Karlsruhe, Germany, Cat. No. K 4300/01) following the manufacturer's instructions. For expression using the T7 regulatory sequences, the construct was transformed into E. coli BL 21 (DE 3) (Studier, F. W., et al, Methods Enzymol. 185 (1990) 60–89) and the transformed bacteria were cultivated in a 1l batch for protein expression.

Purification of His-NNMT fusion protein was done following standard procedures on a Ni-chelate column. Briefly, 1l of bacteria culture containing the expression vector for the His-NNMT fusion protein was pelleted by centrifugation. The cell pellet was resuspended in lysis buffer, containing phosphate, pH 8,0, 7 M guanidium chloride, imidazole and thioglycerole, followed by homogenization using a Ultra-Turrax. Insoluble material was pelleted by high speed centrifugation and the supernatant was applied to a Ni-chelate chromatographic column. The column was washed with several bed volumes of lysis buffer followed by washes with buffer, containing phosphate, pH 8,0 and urea. Finally, bound antigen was eluted using a phosphate buffer containing SDS under acid conditions.

Production of Monoclonal Antibodies Against the NNMT

Immunization of Mice 12 week old A/J mice are initially immunized intraperitoneally with 100 µg NNMT. This is followed after 6 weeks by two further intraperitoneal immunizations at monthly intervals. In this process each mouse is administered 100 µg NNMT adsorbed to aluminum hydroxide and $10^9$ germs of *Bordetella pertussis*. Subsequently the last two immunizations are carried out intravenously on the 3rd and 2nd day before fusion using 100 µg NNMT in PBS buffer for each.

Fusion and Cloning

Spleen cells of the mice immunized according to a) are fused with myeloma cells according to Galfre, G., and Milstein, C., Methods in Enzymology 73 (1981) 3–46. In this process ca. $1*10^8$ spleen cells of the immunized mouse are mixed with $2\times10^7$ myeloma cells (P3X63-Ag8–653, ATCC CRL1580) and centrifuged (10 min at 300 g and 4° C.). The cells are then washed once with RPMI 1640 medium without fetal calf serum (FCS) and centrifuged again at 400 g in a 50 ml conical tube. The supernatant is discarded, the cell sediment is gently loosened by tapping, 1 ml PEG (molecular weight 4000, Merck, Darmstadt) is added and mixed by pipetting. After 1 min in a water-bath at 37° C., 5 ml RPMI 1640 without FCS is added drop-wise at room temperature within a period of 4–5 min. Afterwards 5 ml RPMI 1640 containing 10% FCS is added drop-wise within ca. 1 min, mixed thoroughly, filled to 50 ml with medium (RPMI 1640+10% FCS) and subsequently centrifuged for 10 min at 400 g and 4° C. The sedimented cells are taken up in RPMI 1640 medium containing 10% FCS and sown in hypoxanthine-azaserine selection medium (100 mmol/l hypoxanthine, 1 µg/ml azaserine in RPMI 1640+ 10% FCS). Interleukin 6 at 100 U/ml is added to the medium as a growth factor.

After ca. 10 days the primary cultures are tested for specific antibody. NNMT-positive primary cultures are cloned in 96-well cell culture plates by means of a fluorescence activated cell sorter. In this process again interleukin 6 at 100 U/ml is added to the medium as a growth additive.

Immunoglobulin Isolation from the Cell Culture Supernatants

The hybridoma cells obtained are sown at a density of $1\times10^5$ cells per ml in RPMI 1640 medium containing 10% FCS and proliferated for 7 days in a fermenter (Thermodux Co., Wertheim/Main, Model MCS-104XL, Order No. 144–050). On average concentrations of 100 µg monoclonal antibody per ml are obtained in the culture supernatant. Purification of this antibody from the culture supernatant is carried out by conventional methods in protein chemistry (e.g. according to Bruck, C., et al., Methods in Enzymology 121 (1986) 587–695).

Generation of Polyclonal Antibodies

Immunization

For immunization, a fresh emulsion of the protein solution (100 µg/ml protein NNMT) and complete Freund's adjuvant at the ratio of 1:1 was prepared. Each rabbit was immunized with 1 ml of the emulsion at days 1, 7, 14 and 30, 60 and 90. Blood was drawn and resulting anti-NNMT serum used for further experiments as described in examples 3 and 4.

Purification of IgG (Immunoglobulin G) from Rabbit Serum by Sequential Precipitation with Caprylic Acid and Ammonium Sulfate One volume of rabbit serum was diluted with 4 volumes of acetate buffer (60 mM, pH 4.0). The pH was adjusted to 4.5 with 2 M Tris-base. Caprylic acid (25 µl/ml of diluted sample) was added drop-wise under vigorous stirring. After 30 min the sample was centrifuged (13 000×g, 30 min, 4° C.), the pellet discarded and the supernatant collected. The pH of the supernatant was adjusted to 7.5 by the addition of 2 M Tris-base and filtered (0.2 µm).

The immunoglobulin in the supernatant was precipitated under vigorous stirring by the drop-wise addition of a 4 M ammonium sulfate solution to a final concentration of 2 M. The precipitated immunoglobulins were collected by centrifugation (8000×g, 15 min, 4° C.).

The supernatant was discarded. The pellet was dissolved in 10 mM $NaH_2PO_4$/NaOH, pH 7.5, 30 mM NaCl and exhaustively dialyzed. The dialysate was centrifuged (13 000×g, 15 min, 4° C.) and filtered (0.2 µm).

Biotinylation of Polyclonal Rabbit IgG

Polyclonal rabbit IgG was brought to 10 mg/ml in 10 mM $NaH_2PO_4$/NaOH, pH 7.5, 30 mM NaCl. Per ml IgG solution 50 µl biotin-N-hydroxysuccinimide (3.6 mg/ml in DMSO) were added. After 30 min at room temperature, the sample was chromatographed on SUPERDEX 200 (10 mM $NaH_2PO_4$/NaOH, pH 7.5, 30 mM NaCl). The fraction containing biotinylated IgG were collected. Monoclonal antibodies have been biotinylated according to the same procedure.

Digoxygenylation of Polyclonal Rabbit IgG

Polyclonal rabbit IgG was brought to 10 mg/ml in 10 mM $NaH_2PO_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) were added. After 30 min at room temperature, the sample was chromatographed on SUPERDEX 200 (10 mM $NaH_2PO_4$/NaOH, pH 7.5, 30 mM NaCl). The fractions containing digoxigenylated IgG were collected. Monoclonal antibodies have been labeled with digoxigenin according to the same procedure.

EXAMPLE 3

Western Blotting for the Detection of NNMT in Human Colorectal Cancer Tissue Using Polyclonal Antibody as Generated in Example 2

Tissue lysates from tumor samples and healthy control samples were prepared as described in Example 1, "Tissue preparation".

SDS-PAGE and Western-Blotting were carried out using reagents and equipment of Invitrogen, Karlsruhe, Germany. For each tissue sample tested, 10 µg of tissue lysate were diluted in reducing NUPAGE (Invitrogen) SDS sample buffer and heated for 10 min at 95° C. Samples were run on 4–12% NUPAGE gels (tris-glycine) in the MES running buffer system. The gel-separated protein mixture was blotted onto nitrocellulose membranes using the Invitrogen XCell II Blot Module (Invitrogen) and the NUPAGE transfer buffer system. The membranes were washed 3 times in PBS/0.05% TWEEN 20 and blocked with Roti-Block blocking buffer (A151.1; Carl Roth GmbH, Karlsruhe, Germany) for 2 h. The primary antibody, polyclonal rabbit anti-NNMT serum (generation described in Example 2), was diluted 1:10 000 in Roti-Block blocking buffer and incubated with the membrane for 1 h. The membranes were washed 6 times in PBS/0.05 % TWEEN 20. The specifically bound primary rabbit antibody was labeled with an POD-conjugated polyclonal sheep anti-rabbit IgG antibody, diluted to 10 mU/ml in 0.5×Roti-Block blocking buffer. After incubation for 1 hour, the membranes were washed 6 times in PBS/0.05 % TWEEN 20. For detection of the bound POD-conjugated anti-rabbit antibody, the membrane was incubated with the Lumi-Light$^{pLUS}$ Western Blotting Substrate (Order-No. 2015196, Roche Diagnostics GmbH, Mannheim, Germany) and exposed to an autoradiographic film.

EXAMPLE 4

ELISA for the Measurement of NNMT in Human Serum and Plasma Samples

For detection of NNMT in human serum or plasma, a sandwich ELISA was developed. For capture and detection of the antigen, aliquots of the anti-NNMT polyclonal antibody (see Example 2) were conjugated with biotin and digoxigenin, respectively.

Streptavidin-coated 96-well microtiter plates were incubated with 100 μl biotinylated anti-NNMT polyclonal antibody for 60 min at 10 μg/ml in 10 mM phosphate, pH 7.4, 1% BSA, 0,9% NaCl and 0.1% TWEEN 20. After incubation, plates were washed three times with 0.9% NaCl, 0.1% TWEEN 20. Wells were then incubated for 2 h with either a serial dilution of the recombinant protein (see Example 2) as standard antigen or with diluted plasma samples from patients. After binding of NNMT, plates were washed three times with 0.9% NaCl, 0.1% TWEEN 20. For specific detection of bound NNMT, wells were incubated with 100 μl of digoxygenylated anti-NNMT polyclonal antibody for 60 min at 10 μg/ml in 10 mM phosphate, pH 7.4, 1% BSA, 0,9% NaCl and 0.1% TWEEN 20. Thereafter, plates were washed three times to remove unbound antibody. In a next step, wells were incubated with 20 mU/ml anti-digoxigenin-POD conjugates (Roche Diagnostics GmbH, Mannheim, Germany, Catalog No. 1633716) for 60 min in 10 mM phosphate, pH 7.4, 1% BSA, 0,9% NaCl and 0.1% TWEEN 20. Plates were subsequently washed three times with the same buffer. For detection of antigen-antibody complexes, wells were incubated with 100 μl ABTS solution (Roche Diagnostics GmbH, Mannheim, Germany, Catalog No. 11685767) and OD was measured after 30–60 min at 405 nm with an ELISA reader.

EXAMPLE 5

ROC Analysis to Assess Clinical Utility in Terms of Diagnostic Accuracy

Accuracy was assessed by analyzing individual liquid samples obtained from well-characterized patient cohorts, i.e., 50 patients having undergone colonoscopy and found to be free of adenoma or CRC, 50 patients diagnosed and staged as T1–3, N0, M0 of CRC, and 50 patients diagnosed with progressed CRC, having at least tumor infiltration in at least one proximal lymph node or more severe forms of metastasis, respectively. CEA as measured by a commercially available assay (Roche Diagnostics, CEA-assay (Cat. No. 1173 1629 for ELECSYS Systems immunoassay analyzer) and NNMT measured as described above have been quantified in a serum obtained from each of these individuals. ROC-analysis was performed according to Zweig, M. H., and Campbell, supra. Discriminatory power for differentiating patients in the group T1–3, N0, M0 from healthy individuals as measured by the area under the curve was found to be at least as good for NNMT as compared to the established marker CEA.

Preliminary data indicate that NNMT may also be very helpful in the follow-up of patients after surgery.

---

What is claimed is:

1. A method for diagnosis of human colorectal cancer comprising the steps of:
   a. providing a liquid sample form a patient wherein the sample is selected from the group consisting of serum plasma, and whole blood,
   b. contacting the sample with an antibody or receptor for nicotinamide N-methyltransferase (NNMT) that specifically binds NNMT under conditions appropriate for formation of a complex between the antibody or receptor for NNMT and NNMT,
   c. measuring the amount of complex formed, and
   d. correlating the amount of complex formed to the diagnosis of colorectal cancer.

2. The method of claim 1 wherein the patient is in the adenoma stage.

3. The method of claim 1 wherein the patient is in the $T_{is}$-3 N0 M0 stage.

* * * * *